United States Patent [19]

Fliermans

[11] Patent Number: 4,877,736

[45] Date of Patent: Oct. 31, 1989

[54] AEROBIC MICROORGANISM FOR THE DEGRADATION OF CHLORINATED ALIPHATIC HYDROCARBONS

[75] Inventor: Carl B. Fliermans, Augusta, Ga.

[73] Assignee: The United States of America as represented by the United States Department of Energy, Washington, D.C.

[21] Appl. No.: 256,429

[22] Filed: Oct. 12, 1988

[51] Int. Cl.⁴ ............................................. C12N 9/00
[52] U.S. Cl. .................................... 435/183; 435/262
[58] Field of Search ................ 435/183, 262; 210/600

[56] References Cited

U.S. PATENT DOCUMENTS 4,804,629  2/1989  Roy ...................................... 435/262
4,806,482  2/1989  Horowitz ............................. 435/262
4,808,535  2/1989  Isbister ................................ 435/262
4,816,403  3/1989  Roy ...................................... 435/262

*Primary Examiner*—Peter D. Rosenberg
*Attorney, Agent, or Firm*—Allen F. Westerdahl; Judson R. Hightower

[57] ABSTRACT

A chlorinated aliphatic hydrocarbon-degrading microorganism, having American Type Culture Collection accession numbers ATCC 53570 and 53571, in a biologically pure culture aseptically collected from a deep subsurface habitat and enhanced, mineralizes trichloroethylene and tetrachloroethylene to HCl, $H_2O$ and $CO_2$ under aerobic conditions stimulated by methane, acetate, methanol, tryptone-yeast extract, propane and propane-methane.

18 Claims, 2 Drawing Sheets

AEROBIC MICROORGANISM FOR THE DEGRADATION OF CHLORINATED ALIPHATIC HYDROCARBONS

The United States Government has rights to this invention pursuant to Contract No. DE-AC09-76SR00001 between the U.S. Department of Energy and E. I. DuPont de Nemours & Co.

BACKGROUND OF THE INVENTION

1. Field of the Invention

The invention relates to bacterial degradation of hydrocarbons and, more specifically, to a pure culture of aerobic, mesophilic bacterium capable of biodegrading low-molecular-weight chlorinated, aliphatic hydrocarbons to $CO_2$, HCl and $H_2O$.

2. Discussion of Background and Prior Art

The widespread use of chlorinated aliphatic hydrocarbons, and in particular trichloroethylene (TCE) and tetrachloroethylene (PCE), as solvents, degreasers and ingredients in the manufacture of plastics has resulted in substantial pollution of groundwter. These compounds tend to persist in groundwater.

Currently, to decontaminate groundwater contaminated with TCE and PCE, the groundwater is pumped to the earth's surface where the contaminants are stripped using aeration towers or removed on sorbent. Aerobic biodegradation, on the other hand, is an alternative to surface pumping that holds substantial economic and practical advantages.

Anaerobic bacteria for biodegradation of TCE and PCE are available. Unfortunately, the byproducts of anaerobic biodegradation are vinyl chloride and vinylidene chloride, compounds which are more toxic than their chemical parents. Nontoxic byproducts of the complete biodegradation, or mineralization, of chlorinated aliphatic hydrocarbons, $CO_2$, HCl, and $H_2O$, are obtainable aerobically, but TCE and PCE are resistant to aerobic biodegradation.

Heretofore, conflicting results have been obtained in the search for an aerobic, chlorinated-aliphatic-hydrocarbon degrading bacteria. Some investigators have found no evidence of biodegradation of TCE or PCE. However Tabak, et al., reported the disappearance of over 50% of di-, tri- and tetrachloroethylenes from initial levels of 10 ppm in a period of one week using a mixed sewage innoculum and yeast extract as the primary substrate ("Biodegradability Studies with Organic Priority Pollutant Compounds", 1981, J. Water Pollution Control Federal 53:1503-1518). More recently, Wilson and Wilson found that 150 ppb of TCE was aerobically degraded to carbon dioxide in two days in an unsaturated glass column packed with sandy soil ("Biotransformation of Trichloroethylene in Soil", 1985, Applied and E nvironmental Microbiology, Vol. 49:242–243).

It is known that methanotrohs, methane using organisms, will oxidize and dechlorinate halogenated methanes using the enzyme, methane monooxygenase. It is also known that propane-oxydizing bacteria can epoxidate ethylene and that the epoxide is metabolized further.

Most metanotrophs are capable of utilizing only methane and other C-1 compounds as sole sources of carbon and energy. Methane monooxygenase is a nonspecific enzyme which enables obligate methanotrophs to oxidize a wide variety of nongrowth compounds, including hydroxylation of n-alkanes, epoxidation of n-alkenes, and dechlorination of aliphatic and aromatic substances. Some of these oxidation products, such as n-alkenes, are incorporated into cell material and are considered supplementary substrates.

Since methanotrophs can oxidize ethenes and dechlorinate chloromethanes it seems likely that such bacteria would be able to oxidize chlorinated aliphatic hydrocarbons. However, until the present invention, the search for such bacteria has proved unsuccessful.

SUMMARY OF THE INVENTION

It is an object of the present invention to provide a biologically pure culture of an aerobic bacterium capable of affecting and converting chlorinated aliphatic hydrocarbons to $CO_2$, HCl and $H_2O$.

It is an object of the present invention to provide a biologically pure culture of an aerobic bacterium capable of affecting and mineralizing trichloroethylene and tetrachloroethylene at concentrations above ten parts per billion.

It is a further object of the present invention to provide a biologically pure culture of an aerobic bacterium capable of degrading chlorinated aliphatic hydrocarbons under mesophilic, aerobic conditions.

It is a still further object of the present invention to provide a biologically pure culture of an aerobic bacterium capable of degrading chlorinated aliphatic hydrocarbons without producing vinyl chloride or vinylidene chloride.

It is also an object of the present invention to provide a biologically pure culture of an aerobic bacterium capable of degrading chlorinted aliphatic hydrocarbons in the presence of stimulating substances such as methane, methanol, tryptone-yeast-extract propane or propane-methane.

To achieve the foregoing and other objects and in accordance with the purposes of the invention, as embodied and broadly described herein, the invention involves a biologically pure culture of an aerboic, mesophilic, gram-negative bacterium representative of the strains selected from microorganisms identified by American Type Culture Collection (Rockville, MD, USA) accession numbers ATCC-53570 and ATCC 53571 aseptically extracted from a deep subsurface habitat contaminated for decades by tetrachloroethylene (PCE) and trichloroethylene (TCE) solvent material, isolated and enhanced. These microorganisms have been given the identifying names *Welchia alkenophila* sero 5 (ATCC-53570) and *Welchia alkenophila* sero 33 (ATCC-53571) since they are related to the Welchia genus, are "lovers of alkenes" and are serologically different.

Reference is now made in detail to the present preferred embodiment of the invention, illustrated by the following drawing.

A BRIEF DESCRIPTION OF THE DRAWING

The accompaying drawings, which are incorporated in and form a part of the specification, illustrate the invention and, together with the description, serve to explain the principles of the invention. In the drawing.

DETAILED DESCRIPTION OF THE INVENTION

Figure 1:
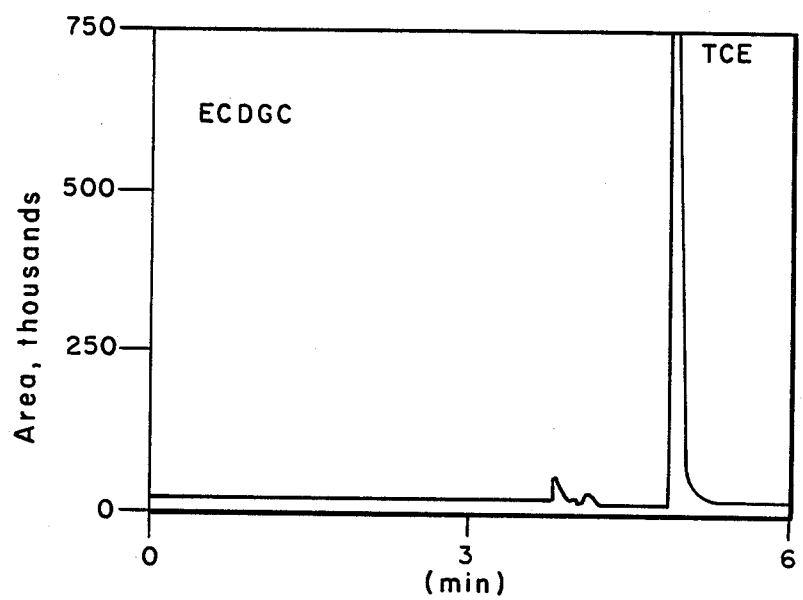
FIG. 1 is a graph showing the biodegradation of TCE according to the present invention with tryptone/yeast extract as a nutrient as measured by carbon-14 presence and percent of carbon dioxide in the atmosphere above the culture.

The microorganism of the present invention was discovered in and aseptically collected from sediment samples found 150 and 190 feet below the soil surface at the Savannah River Plant near Aiken, S.C., USA. Industrial waste effluents from industrial operations have been discharged to process sewers and settling basins since plant startup in 1952.

In 1958 a settling basin for receiving industrial discharges was built and placed in service. Included in these effluents were 3,500,000 pounds of organic solvents, namely TCE, PCE, and 1,1,1-trichloroethane, used for metal degreasing. Although much of these organic solvents evaporated, substantial quantities of the chlorinated aliphatic hydrocarbons seeped into the ground from effluent sewer leaks, the settling basin, and the overflow basin, entering the underlying soil, sediments and groundwater.

The plume of organic contaminants beneath the basin and the effluent sewer has been defined by extensive soil and water sample analysis. Concentrations as high as 500 ppm exist in the plume and as high as 0.2% just beneath the settling basin.

Aseptic sediment samples were collected by split spoon sampling every 10 feet to a depth of 190 feet. The analysis of the samples indicated that the higher concentrations of chlorinated aliphatic hydrocarbons were not nearer to the surface but deeper, at depths of 95 to 145 feet.

It was at the depths corresponding to the higher concentrations, but not the greatest concentrations, that the bacterial strains of the present invention were found, strains that had adapted to an environment in which they were exposed to TCE/PCE for over thirty years. Importantly, the levels of concentration of the organics at those depths exert maximum selective pressure on the bacteria to encourage adaptation to the use of the chlorinated aliphatic hydrocarbons as an energy and carbon source under aerobic conditions. Too great a concentration level is biologically destructive; too small a concentration fails to impose sufficient selectivity pressure for adaptation in the time period available.

The two strains, ATCC 53570 and ATCC 53571, are very similar to each other. Although they are also similar to *Methylomonas albus*, there are several important differences. For example, they do not form cysts; nor do they appear to have a complete TCA cycle or NAD and NAD-dependent isocitrate dehydrogenase.

The new bacteria strains move predominantly by tumbling, having retarded, peritricious flagellation features. These bacteria are large and rod-shaped, 1-2 micrometers in diameter by 7-20 micrometers in length, but often show branching and pointed ends during logarithmic growth. In late logarithmic growth, the bacteria cells may extend several hundred micrometers before dividing into a chain of individual bacterium by the start of te next, stationary, phase of growth.

No spore formation has been observed in ATCC 53570 or ATCC 53571.

The strains are catalase-positive and oxidase-positive. They use methane and $CO_2$ as carbon sources but not monosaccharides and disaccharides. Small levels of yeast extract, about 0.05%, are stimulatory but only in the presence of methane. They hydrolyze gelatin slowly and do not degrade cellulose.

The pH range for these bacterial strains is nominally 4.5-8.5; optimally, 5.5-8.1 Optimum temperature is 23 degrees Celsius and no growth was observed below 12 degrees or above 60 degrees.

To isolate the new strain, subsurface sediment material was collected so as not to disturb or contaminate the microorganisms it might contain. At the depths sampled, a hole was drilled using a thin-walled seamless steel barrel to obtain a sample core.

In order to reduce compression of the core as a result of drag forces on the inner wall of the barrel, a drive shoe, having a slightly smaller outer diameter than the barrel, was attached to the forward end of the barrel. The drive show was fitted with a core-retaining device having spring-loaded teeth that opened as the steel barrel advanced and closed as the barrel was withdrawn.

Processing of the samples in a mobile laborarory was done within minutes after they were obtained. Upon withdrawal of the barrel from the ground, the drive shoe was detached and the sample extruded using a hydraulic jack. In a sterile glove box, the outer 5-8 centimeters of sample core were discarded and a sterile subsample for microbial analysis was obtained from the center of the sample core.

The sterile subsamples were placed in a flow-through chamber containing a modified Foster and Davis mineral salt medium and continually purged for two weeks to six months with a 5%/10%/85% mixture of methane, carbon dioxide and air, respectively, to enhance the bacterial cultures.

The culturing medium for isolating, maintaining, and performing biodegradation experiments with the bacterium consisted of the following (in milligrams/liter): $MgSO_4.7H_2O.200:CACl_2.2H_2O$. $20:NaNO_3.1.000:FeSO_4.7H_2O$. $3.0:KCl.0.07:KH_2PO_4$. $160.0:Na_2HPO_4.184.0:ZnSO_4.7$ $H_2O.0.07:MnCl_2.4H_2O.0.02:H_3BO_4.0.02:CoCl_2.6H_2O$. $0.1:CuCl_2.0.01:NiCl_26H_2O$. $0.02:Na_2MoO_42H_2O$. 0.03: and trace vitamins. 1.0. The final pH was 6.8. When a solid medium was desired, 1.5% Bacto-Agar (Difco Laboratories of Detroit, Mich.) was added. For some experiments, 0.5% yeast extract was added to the Bacto-Agar.

The cultures were maintained in the mineral medium on a platform shaker at 23 degrees Celsius. Serum bottles were capped with "TEFLON" faced silicone septa and sealed with aluminum caps. For newly inoculated cultures, 20 milliliters of air were removed by syringe and replaced with an injection of 20 milliliters of methane. Cultures were sometimes given a supplementary gas consisting of a 2:1 by volume mixture of air and methane. Subculturing was performed weekly. The solid medium plates were incubated in desiccators in 2% methane to 98% air. Stock cultures were maintained on the same mineral medium solidified with 2% Bacto-Agar stored at 4 degrees Celsius.

In the exemplary nutrient medium, methane was the preferred carbon source of the new bacteria. A complex media of methane plus 0.05% tryptone and 0.05% yeast extract stimulated growth compared to pure methane, but monosaccharides such as xylose, ribose, mannose, fructose, glucose and galactose, and disaccharides, such as sucrose, lactose, maltose and cellobiose were not used by these bacterial strains. Growth also did not occur on citrate, tryptophane, mannitol, inositol, sorbitol rhamnose, melibiose, amygdalin and arabinose. The isolates were ONPG negative, arginine dihydrolase negative, lysine decarboxylase negative and ornithin decarboxylase negative. Liquification of gelatin by the bacterium occurs, but very slowly. The strains are gram-negative, catalase-positive, oxidase-positive.

The strains, ATCC 53570 and ATCC 53571, are conveniently cultured using the same nutrient medium as used for isolation in an optimum temperature range of 23-25 degrees Celsius. The doubling time at 23 degrees in about 75 minutes.

Another distinguishing characteristic of ATCC 53570 and ATCC 53571 is their ability to use carbon dioxide and methane as sole carbon and energy sources. As will be shown in specific examples herein, a yield of $CO_2$, HCl, $H_2O$, and auxilliary products from TCE and PCE degradation occurs under totally aerobic conditions without the formation of vinyl chloride or vinylidene chloride. These bacteria strains were able to use methane, methanol, acetate, and glucose as electron donors when added at the rate of 40-16 millimoles of available electron equivalents per liter of media.

To prepare the cultured bacterium samples for testing, fifteen to 25 milliliters of flowing culture and mineral media to a total of 50 milliliters were placed in a 160 milliliter serum bottle and sealed. The control sample consisted of a dupliate culture killed by injecting 1 milliliter of 0.1 grams/milliliter sodium azide solution. Twenty milliliters of air was withdrawn from the serum bottle and replaced with an equivalent volume of methane. Test compounds of 10 to 100 milliliters were injected through the "TEFLON" septa of both experimental and control samples, placed on a shaker for 30 minutes to allow the volatile test compounds to equilibrate between the liquid and gas phases. Next, 1 to 5 milliliters of culture liquid were extracted with a syringe and injected directly into a purge-and-trap vessel on a gas chromatograph. Cultures were inverted during incubation to minimize the potential for leakage. Periodic sampling determined the extent of biodegradation activity, expressed in micromoles of compound degraded per hour per microgram of protein.

The following examples illustrate the invention.

EXAMPLE 1

Cultures established in serum bottles as described above were injected with 20 microliters of a stock solution containing, per milliliter, 58 micrograms of [$C^{14}$] TCE in 40 milligrams of methanol ($5 \times 10^6$ counts per minute) and 218 micrograms of cold TCE in 118 milligrams of 2-propanol. This solution was designed to yield 110 milligrams of TCE per milligram in the liquid culture medium before equilibrium with the headspace of the serum bottle.

Relative amounts of carbon dioxide and radioactive carbon dioxide were determined by gas chromatography-gas proportional counting techniques. The results shown in table 1 demonstrate the ability of the cultures to degrade 50 ppm TCE in the presence of various substrates at the 2-10 micromole level compared to the control samples.

| PERCENT DEGRADATION OF 50 PPM TCE | | | |
|---|---|---|---|
| SUBSTRATE | TEST 1 | TEST 2 | TEST 3 |
| $CH_4$ | 96 | 90 | 86 |
| Acetate | 32 | 35 | 79 |
| Try/YE | 99 | 50 | 30 |
| Methanol | 99 | 34 | 43 |
| Propane | 38 | 57 | 20 |
| Propane/$CH_4$ | 30 | 75 | 40 |

EXAMPLE 2

Cultures isolated as described in Example 1 were screened for their abilities to use various electron donors in the degradation of various concentrations of TCE. Sealed tubes containing 40-60 millimoles of electron donor per liter were injected with 50, 150, and 300 ppm TCE. The control samples were inhibited with formalin at the start of the experiment. The results, in terms of a percentage of degradation over the control samples, are shown in Table 2.

| EFFECT OF ELECTRON DONORS ON PERCENT DEGRADATION OF TCE | | | |
|---|---|---|---|
| DONOR | 50 PPM | 150 PPM | 300 PPM |
| Try/YE | 98 | 37 | 0 |
| Glucose | 93 | 18 | 0 |
| Acetate | 99 | 24 | 0 |
| Methanol | 99 | 0 | 0 |
| TCE | 0 | 0 | 0 |
| $H_2:CO_2$ | 0 | 0 | 0 |
| Propane | 0 | 8 | 0 |
| Methane | 91 | 23 | 0 |

Typical cultures were capable of degrading TCE at the 50 ppm level to an extent greater than 99.8%. At the 150 ppm level, TCE consumption would vary up to 50%. The upper limit of TCE degradation appears to be 200 ppm; the upper limit of TCE tolerance is about 300 ppm.

EXAMPLE 3

Duplicate vials containing the bacterial strains were inoculated with 30 ppm TCE plus 700,000 disintegrations per minute of $C^{14}$—1,1,2 TCE in three milliliters medium per 12 milliliter vial. The vials were then incubated for three weeks at 23 degrees Celsius. Loss of total TCE was measured by purge and trap analysis using an electron capture detector.

Figure 2:
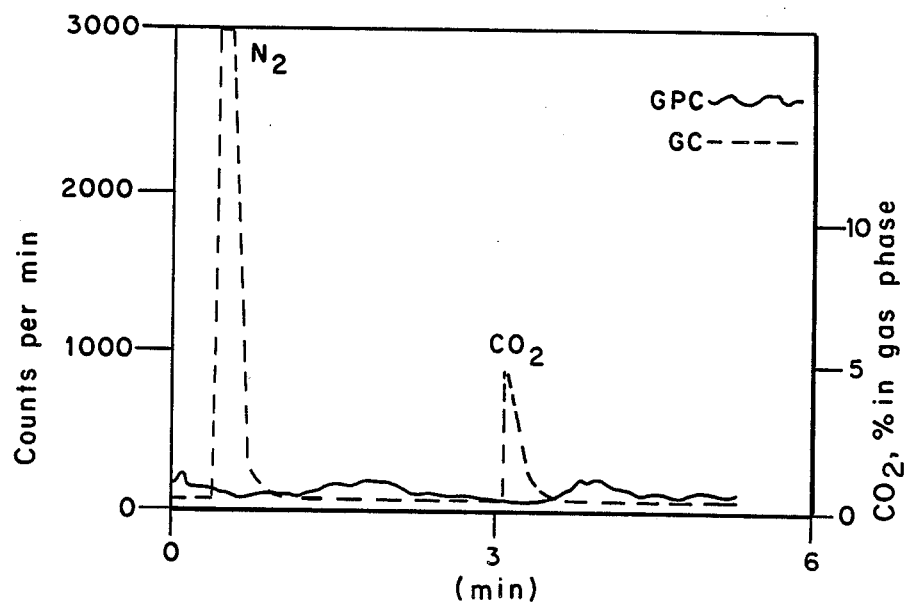
FIG. 2 is a graph showing the biodegradataion of TCE according to the present invention with tryptone/yeast extract as a nutrient as measured by the amount of TCE in a sample culture.
Figure 3:
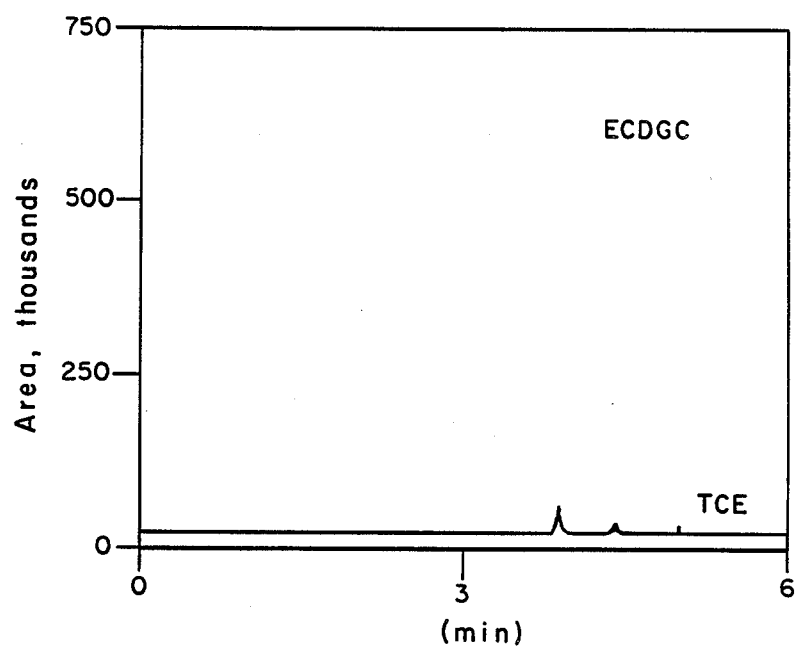
FIG. 3 is a graph showing the biodegradation of TCE according to the present invention with methanol as a nutrient as measured by carbon-14 presence and percent of carbon dioxide in the atmosphere above the culture.
Figure 4:
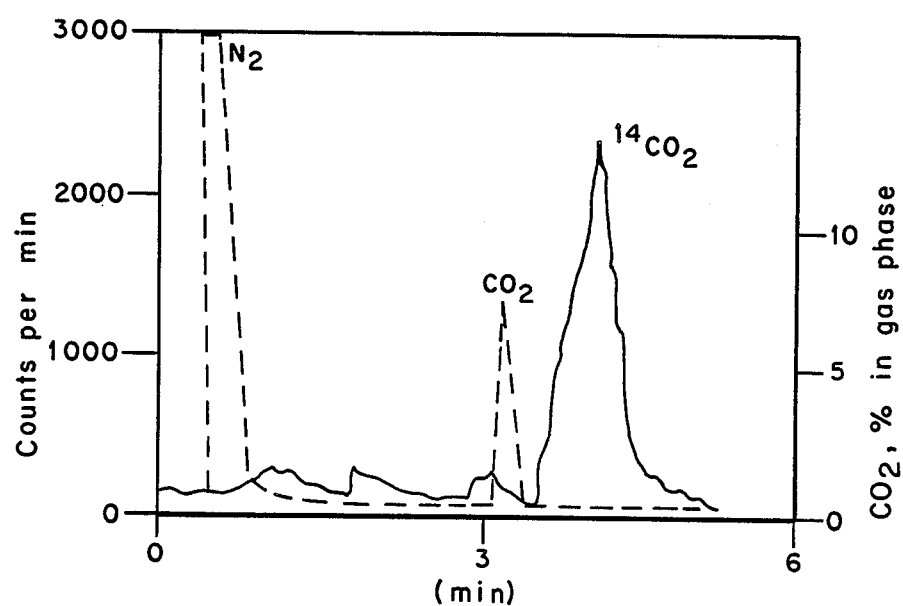
FIG. 4 is a graph showing the biodegradation of TCE according to the present invention with methanol as a nutrient as measured by the amount of TCE in a sample culture.

The results are graphed in FIGS. 1, 2, 3 and 4. FIGS. 1 and 3 show the change in the amount of radioactive carbon dioxide present as measured by gas proportional counting instrumentation and by gas chromatography in the presence of tryptone/yeast extract and methanol, respectively. FIGS. 2 and 4 show the decrease in TCE (measured in units proportional top the amount of TCE) with time by an electron capture detector, the bacterium in the presence of tryptone/yeast extract and methanol, respectively.

Greater than 99% of TCE in several tubes was degraded in addition to the production of dichloroethylene. Gas chromatography revealed evidence of metabolism by the increase of total carbon dioxide in the atmosphere of the headspace of the serum bottles. Importantly, radioactive carbon dioxide, quantified by gas proportional counting confirms TCE was consumed and carbon dioxide was produced. Over 40% of the radioactive TCE was accounted for by the carbon dioxide and no formation of vinyl chloride or vinylidene chloride was observed. The results demonstrate that these new bacteria strains use a variety of electron donor and are capable of converting TCE to carbon dioxide.

The foregoing description of the preferred embodiment of the invention has been presented for purposes of illustration and description. It is not intended to be exhaustive or to limit the invention to the precise form disclosed. The embodiment was chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. A biologically pure culture of a microorganism having the identifying characteristics of a representative strain selected from the group consisting of *Welchia alkenophila* sero 5 of ATCC 53570 and *Welchia alkenophila* sero 33 of ATCC 53571.

2. The biologically pure culture of claim 1, said culture being capable of effecting degradation of chlorinated aliphatic hydrocarbons without the formation of vinyl chloride or vinylidene chloride.

3. The biologically pure culture of claim 2 wherein said degradation is effected under mesophilic, aerobic conditions.

4. The biologically pure culture of claim 2, wherein said chlorinated aliphatic hydrocarbons are selected from the group consisting of trichloroethylene and tetrachloroethylene.

5. The biologically pure culture of claim 2, wherein said degradation is stimulated by a nutrient medium selected from the group consisting essentially of methane, methanol, acetate, tryptone-yeast extract, propane and propane-methane.

6. The biologically pure culture of claim 1, said culture having the ability to degrade chlorinated aliphatic hydrocarbons to carbon dioxide, without the formation of vinyl chloride or vinylidene chloride.

7. A mesophilic, aerobic, gram negative bacterium having the identifying characteristics of a representative strain selected from the group consisting of *Welchia alkenophila* sero 5 of ATCC 53570 and *Welchia alkenophila* sero 33 ATCC 53571 in a biologically pure culture.

8. An enzymatically activated material produced by the microorganism having the identifying characteristics of a representative strain selected from the group consisting of *Welchia alkenophila* sero 5 ATCC 53570 and *Welchia alkenophila* sero 33 ATCC 53571, said material being capable of effecting the degradation of chlorinated aliphatic hydrocarbons without the formation of vinyl chloride or vinylidene chloride.

9. A method of effecting degradation of a chlorinated aliphatic hydrocarbon without the formation of vinyl chloride or vinyldene chloride which comprises application of a microorganism having the identifying characteristics of a representative strain selected from the group consisting of *Welchia alkenophila* sero 5 of ATCC 53570 and *Welchia alkenophila* sero 33 of ATCC 53571 to a chlorinated aliphatic hydrocarbon in the presence of a nutrient medium.

10. The method of claim 9, wherein said chlorinated aliphatic hydrocarbon is selected from the group consisting essentially of trichloroethylene and tetrachloroethylene.

11. The method of claim 9, wherein said nutrient medium is selected from the group consisting of methane, acetate, methanol, tryptone-yeast-extract, propane and propane-methane.

12. The method of claim 10, wherein said nutrient medium is selected from the group consisting essentially of methane, acetate, methanol, tryptone-yeast-extact, propane and propane-methane.

13. The method of claim 9 which comprises cultivating the microorganism in the presence of chlorinated aliphiatic hydrocarbons and a nutrient medium under aerobic conditions to effect degradation of said hydrocarbons.

14. The method of claim 13, wherein said hydrocarbons are selected from the group consisting essentially of trichloroethylene and tetrachloroethylene and wherein said nutrient medium is selected from the group consisting of methane, acetate, methanol tryptone-yeast-extract, propane and propane-methane.

15. The method of claim 14 wherein the cultivation of the microorganism takes place under aerobic conditions.

16. The method of claim 15 wherein degradation of said hydrocarbons yield essentially $CO_2$, HCl and $H_2O$.

17. the method of claim 14 wherein the cultivation of the microorganism takes place in a temperature range of approximately 23 to 25 degrees Celsius.

18. The method of claim 14 wherein the cultivation of the microorganism takes place in a pH range of approximately 5.5 to 8.1.

* * * * *